United States Patent
Kakiuchi et al.

(10) Patent No.: US 10,173,958 B2
(45) Date of Patent: Jan. 8, 2019

(54) METHOD FOR PRODUCING MULTIBRANCHED ALIPHATIC ESTER

(71) Applicant: NISSAN CHEMICAL INDUSTRIES, LTD., Tokyo (JP)

(72) Inventors: Nobuyuki Kakiuchi, Funabashi (JP); Takaomi Fushimi, Tokyo (JP); Mituyosi Ohata, Ichihara (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 0 days.

(21) Appl. No.: 15/313,506

(22) PCT Filed: May 20, 2015

(86) PCT No.: PCT/JP2015/064483
§ 371 (c)(1),
(2) Date: Nov. 22, 2016

(87) PCT Pub. No.: WO2015/186522
PCT Pub. Date: Dec. 10, 2015

(65) Prior Publication Data
US 2017/0197902 A1    Jul. 13, 2017

(30) Foreign Application Priority Data

Jun. 4, 2014  (JP) ................................. 2014-115902

(51) Int. Cl.
*C07C 67/08* (2006.01)
*C07C 67/54* (2006.01)
*C07C 69/24* (2006.01)

(52) U.S. Cl.
CPC .............. *C07C 67/08* (2013.01); *C07C 67/54* (2013.01); *C07C 69/24* (2013.01)

(58) Field of Classification Search
CPC ..................................................... C07C 67/08
See application file for complete search history.

(56) References Cited

U.S. PATENT DOCUMENTS

| | | | | |
|---|---|---|---|---|
| 3,734,951 A | * | 5/1973 | Suter et al. | C07C 67/08 560/193 |
| 4,332,738 A | * | 6/1982 | Benitez | C07C 67/08 554/101 |
| 5,711,939 A | * | 1/1998 | Brunke | A61Q 19/00 424/59 |
| 6,939,980 B2 | * | 9/2005 | Memita | C07C 67/58 554/170 |

FOREIGN PATENT DOCUMENTS

| | | |
|---|---|---|
| JP | S47-29495 B1 | 8/1972 |
| JP | S49-48615 A | 5/1974 |
| JP | S50-4021 A | 1/1975 |
| JP | S50-7789 A | 1/1975 |
| JP | S52-87113 A | 7/1977 |
| JP | S52-102203 A | 8/1977 |
| JP | S58-220874 A | 12/1983 |
| JP | S63-101346 A | 5/1988 |
| JP | H03-77846 A | 4/1991 |
| JP | H05-502668 A | 5/1993 |
| JP | H09-87435 A | 3/1997 |
| JP | 2004-026738 A | 1/2004 |
| JP | 2005-206573 A | 8/2005 |
| JP | 2006-265114 A | 10/2006 |
| JP | 2008-013546 A | 1/2008 |
| JP | 2012-512154 A | 5/2012 |
| WO | 02/22548 A1 | 3/2002 |

OTHER PUBLICATIONS

Zaragoza Dorwald, Side Reactions in Organic Synthesis, Wiley-VCH Verlag GmbH & Co. KGaA, Weinheim, Preface. p. IX.*
Aug. 18, 2015 International Search Report issued in International Patent Application No. PCT/JP2015/064483.
Aug. 18, 2015 Written Opinion of the International Searching Authority issued in International Patent Application No. PCT/JP2015/064483.

* cited by examiner

*Primary Examiner* — Paul A Zucker
(74) *Attorney, Agent, or Firm* — Oliff PLC

(57) ABSTRACT

A method for producing a multibranched aliphatic ester including reacting a multibranched aliphatic alcohol with a multibranched aliphatic carboxylic acid in the absence of a solvent without a catalyst to obtain a multibranched aliphatic ester, and distilling the multibranched aliphatic ester to obtain a purified multibranched aliphatic ester, wherein at least one of the alcohol and the carboxylic acid is a $C_{10\text{-}30}$ compound, and the obtained ester has a Hazen color number (APHA) of 1 to 30. Each of the multibranched aliphatic alcohol and the multibranched carboxylic acid has a tertiary carbon atom and/or a quaternary carbon atom in the molecule and in which the total number of the tertiary carbon atom and/or the quaternary carbon atom in the molecule is 2 or more. The method wherein the reaction is caused at 180 to 300° C. The method wherein a monohydric alcohol and a monovalent carboxylic acid are used.

11 Claims, No Drawings

US 10,173,958 B2

METHOD FOR PRODUCING MULTIBRANCHED ALIPHATIC ESTER

TECHNICAL FIELD

The present invention relates to a method for producing a multibranched aliphatic ester having high transparency.

BACKGROUND ART

A method for producing an aliphatic ester having a low degree of coloration has been investigated. A higher aliphatic ester has been used in various applications such as cosmetics, lubricants, dispersants, and viscosity modifiers, and in particular, a higher aliphatic ester having low coloration property is desired in the application of cosmetics.

For example, a method for producing an ester comprising reacting a polyhydric alcohol with a saturated aliphatic monocarboxylic acid or a derivative thereof; wherein in the reaction, the saturated aliphatic monocarboxylic acid or the derivative thereof is further added so that the amount of the polyhydric alcohol is 1/1.1 to 1/1.5 relative to the whole amount of the saturated aliphatic monocarboxylic acid or the derivative thereof has been investigated (see Patent Document 1). In this method, the reaction is carried out without a catalyst in the absence of a solvent.

A method for producing an ester comprising the steps of reacting an alcohol with a carboxylic acid to obtain a crude esterified product, adding a hydrocarbon solvent to the crude esterified product, and removing the carboxylic acid excessively added or the like using an aqueous alkaline solution is disclosed (see Patent Document 2). Examples of the alcohol include linear $C_{5-30}$ alcohols. Further, examples thereof include branched alcohols such as 3,5,5-trimethylhexanol and isononanol. Examples of branched carboxylic acid include 3,5,5-trimethylhexanoic acid and isononanoic acid.

A slippage preventing agent containing, as a component, isostearyl isostearate that is obtained by esterification of isostearyl alcohol with isostearic acid is disclosed (see Patent Document 3). Industrial production by an esterification reaction of isostearyl alcohol or isostearic acid used herein with another acid or alcohol is described (see Patent Document 4).

A method for producing a higher aliphatic ester having an α-β branching or neo structure comprising producing a higher alcohol boric acid ester from a higher $C_{10\text{-}}$ alcohol that has or does not have an α-β branching or neo structure and a boric acid esterifying agent and causing a transesterification reaction of the boric acid ester with a higher $C_{10\text{-}}$ fatty acid that having an α-β branching or neo structure is disclosed (see Patent Document 4).

PRIOR ART DOCUMENTS

Patent Documents

Patent Document 1: Japanese Patent Application Publication No. 2008013546 (JP 2008-013546 A)
Patent Document 2: International Publication No. WO 2002/022548
Patent Document 3: Japanese Patent Application Publication No. 50-7789 (JP 50-7789 A)
Patent Document 4: Japanese Patent Application Publication No. 4948615 (JP 49-48615 A)

SUMMARY OF THE INVENTION

Problem to be Solved by the Invention

Conventionally, a higher aliphatic ester is produced from a higher aliphatic alcohol and a higher aliphatic carboxylic acid by addition of an acid catalyst in a solvent. However, in the obtained higher aliphatic ester, coloration occurs. Even when the higher aliphatic ester as a product is distilled, coloration cannot be removed from the product.

In the present invention, when among higher aliphatic alcohols and carboxylic acids, a multibranched aliphatic alcohol and a multibranched aliphatic carboxylic acid are used, a reaction advances in the absence of a solvent without a catalyst, to obtain a multibranched aliphatic ester. The product has a sufficiently low value of coloration property that is represented by Hazen color number (APHA). However, it is found that when the product is removed by distillation, a multibranched aliphatic ester having a still lower Hazen color number (APHA) is obtained.

A method for producing a multibranched aliphatic ester having a low Hazen color number (APHA) by reacting a multibranched aliphatic alcohol with a multibranched aliphatic carboxylic acid in the absence of a solvent without a catalyst is provided.

Means for Solving the Problems

A first aspect of the present invention is a method for producing a multibranched aliphatic ester comprising reacting a multibranched aliphatic alcohol with a multibranched aliphatic carboxylic acid in the absence of a solvent without a catalyst to obtain a multibranched aliphatic ester, and distilling the multibranched aliphatic ester to obtain a purified multibranched aliphatic ester, wherein at least one of the alcohol and the carboxylic acid is a $C_{10-30}$ compound, and the obtained ester has a Hazen color number (APHA) of 1 to 30.

A second aspect is the method according to the first aspect, wherein a multibranched aliphatic $C_{10-30}$ alcohol is reacted with a multibranched aliphatic $C_{7-30}$ carboxylic acid to obtain a multibranched aliphatic $C_{17-60}$ ester.

A third aspect is the method according to the first aspect, wherein a multibranched aliphatic $C_{7-30}$ alcohol is reacted with a multibranched aliphatic $C_{10-30}$ carboxylic acid to obtain a multibranched aliphatic $C_{17-60}$ ester.

A fourth aspect is the method according to the first aspect, wherein a multibranched aliphatic $C_{10-30}$ alcohol is reacted with a multibranched aliphatic $C_{10-30}$ carboxylic acid to obtain a multibranched aliphatic $C_{20-60}$ ester.

A fifth aspect is the method according to any one of the first to fourth aspects, wherein the multibranched aliphatic carboxylic acid is reacted in an amount of 0.8 to 2.5 mol relative to 1 mol of the multibranched aliphatic alcohol.

A sixth aspect is the method according to any one of the first to fifth aspects, wherein each of the multibranched aliphatic alcohol and the multibranched carboxylic acid has a tertiary carbon atom and/or a quaternary carbon atom in the molecule and in which the total number of the tertiary carbon atom and/or the quaternary carbon atom in the molecule is 2 or more.

A seventh aspect is the method according to any one of the first to fifth aspects, wherein each of the multibranched aliphatic alcohol and the multibranched carboxylic acid has a tertiary carbon atom and/or a quaternary carbon atom in the molecule and in which the total number of the tertiary carbon atom and/or the quaternary carbon atom in the molecule is 2 to 10.

An eighth aspect is the method according to any one of the first to seventh aspects, wherein the multibranched aliphatic alcohol is a monohydric alcohol.

A ninth aspect is the method according to any one of the first to seventh aspects, wherein the multibranched aliphatic alcohol is isostearyl alcohol, isoarachidyl alcohol, or trimethylhexyl alcohol.

A tenth aspect is the method according to any one of the first to ninth aspects, wherein the multibranched aliphatic carboxylic acid is a monovalent carboxylic acid.

An eleventh aspect is the method according to any one of the first to ninth aspects, wherein the multibranched aliphatic carboxylic acid is isostearic acid, isoarachidic acid, or trimethylhexanoic acid.

A twelfth aspect is the method according to any one of the first to eleventh aspects, wherein the reaction is carried out at 180 to 300° C.

A thirteenth aspect is the method according to any one of the first to twelfth aspects, wherein the Hazen color number (APHA) is 1 to 20.

A fourteenth aspect is an ester of the following Formula (1-1) or (1-2).

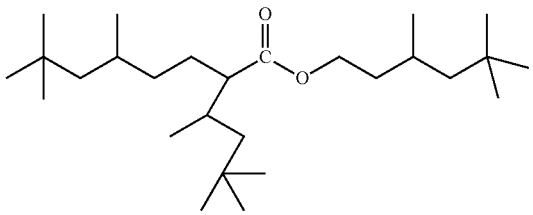

Formula (1-1)

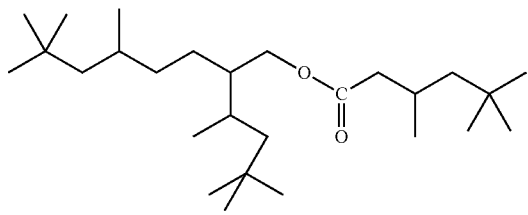

Formula (1-2)

Effects of the Invention

In the present invention, when among higher aliphatic alcohols and carboxylic acids, a multibranched aliphatic alcohol and a multibranched aliphatic carboxylic acid are used as raw materials to produce a multibranched higher aliphatic ester, an esterification reaction advances in the absence of a solvent without a catalyst to obtain the multibranched higher aliphatic ester.

A method in which a multibranched aliphatic $C_{10-30}$ alcohol as a raw material alcohol is reacted with a multibranched aliphatic $C_{7-30}$ carboxylic acid as a raw material carboxylic acid to obtain a multibranched aliphatic $C_{17-60}$ ester, a method in which a multibranched aliphatic $C_{7-30}$ alcohol is reacted with a multibranched aliphatic $C_{10-30}$ carboxylic acid to obtain a multibranched aliphatic $C_{17-60}$ ester, and a method in which a multibranched aliphatic $C_{10-30}$ alcohol is reacted with a multibranched aliphatic $C_{10-30}$ carboxylic acid to obtain a multibranched aliphatic $C_{20-60}$ ester are exemplified.

Namely, the method of the present invention can be applied to a case where at least one of the alcohol and the carboxylic acid is a multibranched higher aliphatic $C_{10-30}$ compound.

In the present invention, even when a catalyst such as an acid compound is used, the reaction advances at relatively lower temperature (about 120 to about 150° C.). However, although the reaction is carried out at lower temperature, a component obtained by decomposition of the acid catalyst (sulfonic acid, etc.) remains in the obtained multibranched higher aliphatic ester, and the ester as a product is colored. In the colored ester, coloration is not eliminated even by distillation. It is considered that a coloration component is strongly interacted with the ester and cannot be removed even by distillation.

The ester obtained by the present invention shows a low Hazen color number (APHA). However, such an effect is not achieved when an alcohol and a carboxylic acid having a low branching degree are used. For example, a linear higher aliphatic alcohol and a linear higher aliphatic carboxylic acid have low thermal stability, a decomposition product of linear chain component thereof is strongly interacted with the ester as a product, and the obtained ester cannot be made sufficiently transparent by distillation or the like. Therefore, it is considered that the ester is colored.

At least one of the alcohol and the carboxylic acid used in the present invention is a $C_{10-30}$ compound. The $C_{10-30}$ compound has a property of a reactive solvent. Therefore, one or both of the alcohol and the carboxylic acid is considered to serve as a solvent in a reaction system. Accordingly, the alcohol and the carboxylic acid are made soluble in each other to form a uniform reaction system. Thus, the reaction advances.

The alcohol and the carboxylic acid of the present invention have a carbon atom number of 10 to 30, and a tertiary carbon atom or a quaternary carbon atom showing a branching degree is present so that the number thereof becomes a specific value. For this reason, the alcohol and the carboxylic acid have high thermal stability and high mutual solubility. Therefore, the reaction sufficiently advances even without addition of a catalyst. Accordingly, an ester having a lower Hazen color number (APHA) (that is, having low coloration property) as compared with an ester as a conventional product is obtained.

In the present invention, by selecting specific raw materials and carrying out a reaction in the absence of a solvent without a catalyst, an ester obtained is not almost colored. Therefore, the ester obtained by the present invention can be effectively used in an application in which a colored ester compound is undesired, for example, fields of cosmetics, coatings, and lubricants.

In the present invention, when the amount of the carboxylic acid is larger than that of the alcohol in an equivalent weight ratio, the carboxylic acid as the raw material may exert a catalytic effect.

The present invention is a method in which specific alcohol and carboxylic acid as raw materials are selected to promote a reaction in the absence of a solvent without a catalyst, and as a result, an ester having a low Hazen color number (APHA) (that is, high transparency) is obtained.

MODES FOR CARRYING OUT THE INVENTION

The present invention is a method for producing a multibranched aliphatic ester by reacting a multibranched aliphatic alcohol with a multibranched aliphatic carboxylic acid in the absence of a solvent without a catalyst, wherein at least one of the alcohol and the carboxylic acid is a $C_{10-30}$ compound, and the obtained ester has a Hazen color number (APHA) of 1 to 30 or 1 to 20.

The Hazen color number (APHA) is measured by a method of testing the color of a liquid chemical product at normal temperature or a chemical product to be melted by heating. The method is described in Japanese Industrial Standards JIS K0071-1 or International Standard ISO/DIS6271. In the present invention, the Hazen color number is used in measurement of color of a liquid ester at normal temperature. As a principle, the color of the liquid chemical product is compared with a standard matching solution (platinum-cobalt standard matching solution), and a result thereof is represented in Hazen unit color number.

The measurement of Hazen color number is evaluated by comparing the standard solution with a sample by the unaided eye in Japanese Industrial Standards. However, in the present invention, the measurement can be evaluated by a measurement device.

The evaluation by visual check may be different from the evaluation obtained by measurement of Hazen color number using a photoelectric meter or a spectrophoto meter since light absorption curves and refractive indices may be different in comparison of the Hazen standard color with the sample. In order to prevent the different result, a Hazen color number measurement device in which a measurement value in accordance with evaluation by the unaided eye can be obtained on the basis of the principle of a photoelectric colorimeter can be used. For example, product name HM-IV manufactured by X DENSHI SEKKEI, K. K., can be used.

In the present invention, a method for producing a multibranched aliphatic $C_{7-60}$ ester by reacting a multibranched aliphatic $C_{10-30}$ alcohol with a multibranched aliphatic $C_{7-30}$ carboxylic acid is exemplified.

A method for producing a multibranched aliphatic $C_{17-60}$ ester by reacting a multibranched aliphatic $C_{7-30}$ alcohol with a multibranched aliphatic $C_{10-30}$ carboxylic acid is exemplified.

A method for producing a multibranched aliphatic $C_{20-60}$ ester by reacting a multibranched aliphatic $C_{10-30}$ alcohol with a multibranched aliphatic $C_{10-30}$ carboxylic acid is exemplified. Therefore, when a $C_{10-30}$ compound is used as at least one of the alcohol and the carboxylic acid, the method is achieved.

As the multibranched aliphatic alcohol and the multibranched aliphatic carboxylic acid, a multibranched aliphatic alcohol and a multibranched aliphatic carboxylic acid each of which has a tertiary carbon atom and/or a quaternary carbon atom in the molecule and in which the total number of the carbon atoms in the molecule is 2 or more, 3 or more, or 5 or more can be used.

As the multibranched aliphatic alcohol and the multibranched aliphatic carboxylic acid, a multibranched aliphatic alcohol and a multibranched aliphatic carboxylic acid each of which has a tertiary carbon atom and/or a quaternary carbon atom in the molecule and in which the total number of the carbon atoms in the molecule is 2 to 10, 3 to 10, 5 to 10, or 2 to 5 can be used.

As the multibranched aliphatic alcohol and the multibranched aliphatic carboxylic acid, a multibranched aliphatic alcohol and a multibranched aliphatic carboxylic acid each of which has a tertiary carbon atom and a quaternary carbon atom in the molecule and in which the total number of the carbon atoms in the molecule is 2 to 10, 3 to 10, 5 to 10, or 2 to 5 can be used.

As the multibranched aliphatic alcohol, a monohydric alcohol can be used. Examples thereof include isostearyl alcohol (having a carbon atom number of 18), isoarachidyl alcohol (having a carbon atom number of 20), and trimethylhexyl alcohol (having a carbon atom number of 9).

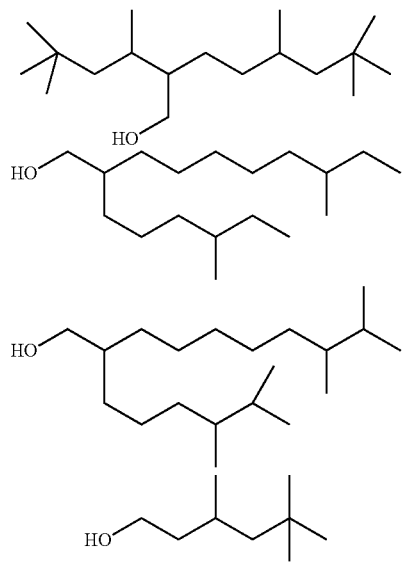

As the multibranched aliphatic carboxylic acid, a monovalent carboxylic acid can be used. Examples thereof include isostearic acid (having a carbon atom number of 18), isoarachidic acid (having a carbon atom number of 20), and trimethylhexanoic acid (having a carbon atom number of 9).

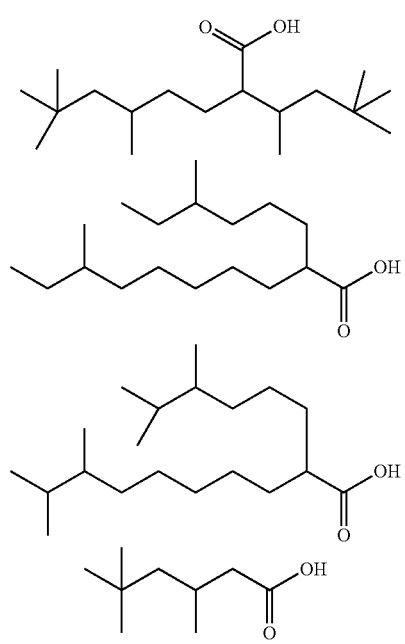

It is preferable that the alcohol and the carboxylic acid be monovalent compounds. When divalent or trivalent compounds are used, polymerization advances to produce polyester. Thus, an ester suitable for an application cannot be obtained.

The ester is obtained by the reaction under a condition of producing the ester including at a temperature of 180 to 300° C. or 200 to 260° C. for 1 to 40 hours or 4 to 25 hours.

The multibranched aliphatic alcohol can be reacted with the multibranched aliphatic carboxylic acid at a ratio of the carboxylic acid of 0.8 to 2.5 mol, preferably 1.01 to 2.5 mol, and preferably 1.01 to 1.3 mol, relative to 1 mol of the alcohol.

As a reaction vessel, a container equipped with a stirrer and a reflux device is used. Nitrogen can be drained by a flowing device of nitrogen or the like. A produced water by dehydration of an esterification reaction can be separated. As the container, a pressure-resistant container can be used.

Examples of the container used in the reaction include a stainless steel reaction vessel and a glass lining reaction vessel in which the inside of a stainless steel container is coated with glass. When the stainless steel reaction vessel is used, a component from stainless steel can be eluted at a reaction process. Therefore, it is preferable that the glass lining reaction vessel be used in order to obtain, a product having low coloration property without a decrease in purity.

Examples of the ester obtained by the present invention include the following.

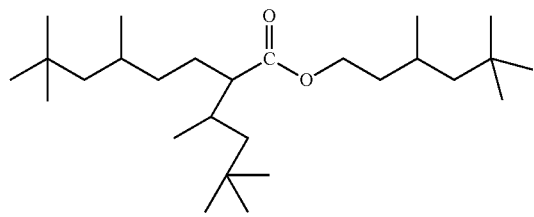

Formula (1-1)

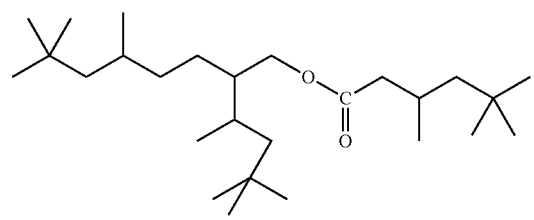

Formula (1-2)

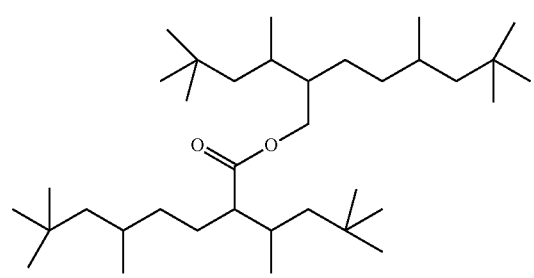

Formula (1-3)

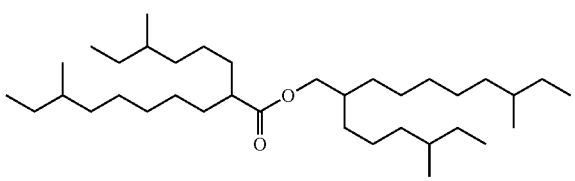

Formula (1-4)

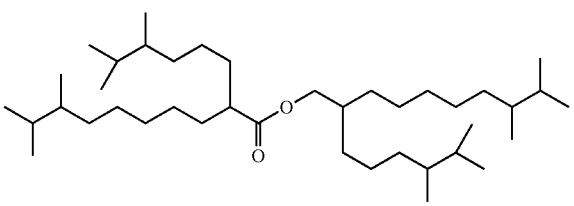

Formula (1-5)

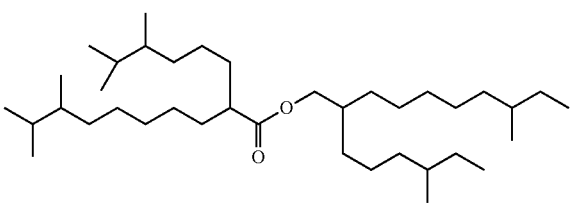

Formula (1-6)

At that time, the ester obtained from the alcohol and the carboxylic acid has a Hazen color number (APHA) of about 30 to 80.

In the method, the ester having the decreased Hazen color number (APHA) of 1 to 30, 1 to 20, 1 to 10, or 1 to 6 can be obtained by distillation. For example, the ester having a Hazen color number of 4 to 30, 4 to 20, or 4 to 10 is obtained.

In the ester having a low molecular weight, general distillation under reduced pressure is carried out as the distillation. In the ester having a high molecular weight, thin film distillation, short-process distillation, molecular distillation, or the like can be used. The distillation condition may be, for example, a temperature of 80 to 300° C. and a degree of reduced pressure of 0.05 to 50 Pa.

The present invention is a novel ester of Formula (1-1) or (1-2).

EXAMPLES

Devices used for analysis of samples are as follows.
GC (Gas Chromatography)
Device: GC-2010 Plus system manufactured by SHIMADZU CORPORATION (analysis of purity)
Hazen Meter
Device: HM-IV manufactured by X DENSHI SEKKEI, K. K. (analysis of hue APHA)

A light source of the measurement device was a three-color LED. A light receiving element was a silicon photodiode.

Hazen calculation processing was carried out by a internal system of the device, and the Hazen color number was displayed. The measurement was carried out within a measuring range of Hazen color number of 0 to 1,000 at an accuracy of Hazen color number within ±2 by comparison with a standard solution having a Hazen color number of 10 to 1,000. About 20 mL of measurement sample was placed in a hard glass test tube as a sample cell and measurement was carried out.
NMR
Device: JNM-ECP300 manufactured by JEOL Ltd.
GC-MS
Device: GCMS-QP2010 Ultra manufactured by SHIMADZU CORPORATION
ICP-OES
Device: SPS-5520 manufactured by SII (SEIKO INSTRUMENTS Inc.)

Example 1/Reaction without Catalyst in the Absence of Solvent 540 g of isostearyl alcohol (5,7,7-trimethyl 2-[1,3,3-trimethylbutyl]octanol-1 (trade name FO-180 available from NISSAN CHEMICAL INDUSTRIES, LTD., APHA=4)) and 596 g of isostearic acid (5,5,7-trimethyl 2-[1,3,3-trimethylbutyl]octanoic acid-1 (available from NISSAN CHEMICAL INDUSTRIES, LTD., APHA=8)) were placed in a stainless steel reactor, and reacted at 250° C. for 21 hours under nitrogen flow. As a result, 1,066 g of crude product of isostearyl isostearate (corresponding to Formula (1-3)) as a corresponding ester body was obtained. As a result of GC analysis, the amount of isostearyl isostearate was 87.6%, the amount of isostearyl alcohol was 6.3%, the amount of isostearic acid was 5.5%, and the total amount of other components was 0.6%. At that time, APHA was 29.

1,000 g of the crude product was purified by distillation using a short-process distillation device (roller wiper-type). Remaining isostearyl alcohol and isostearic acid were distilled at a temperature of 140° C. and a degree of reduced pressure of 6.6 to 8.6 Pa. As a result, 790 g of isostearyl isostearate as a residue was obtained. As a result of GC analysis, the amount of isostearyl isostearate was 98.6%, the amount of isostearyl alcohol was 0.1%, the amount of isostearic acid was 1.0%, and the total amount of other components was 0.3%. At that time, APHA was 38.

From the Obtained residue, isostearyl isostearate was distilled at a temperature of 150° C. and a degree of reduced pressure of 0.1 Pa by the distillation device. The amount of the resultant colorless transparent isostearyl isostearate was 735 g. As a result of GC analysis, the amount of isostearyl isostearate was 99.3%, the amount of isostearic acid was 0.3%, and the total amount of other components was 0.4%. At that time, APHA was 9. As a result of ICP analysis, iron was not detected. In the residue, a slight amount of coloration component mixed from the stainless steel reactor during the reaction remained, the residue was brown, and APHA thereof was 498. As the result of ICP analysis, 13 ppm of iron was detected.

Example 2/Reaction without Catalyst in the Absence of Solvent

Isostearyl isostearate was synthesized by the same procedure as in Example 1 using a glass lining reactor as the reactor, The crude product was purified using a general distillation device. Isostearyl isostearate (corresponding to Formula (1-3)) was distilled at a temperature of 270 to 280° C. and a degree of reduced pressure of 0.1 Pa to obtain a colorless transparent target. As a result of GC analysis, the amount of isostearyl isostearate was 99.8%, and the amount of isostearic acid was 0.2%. APHA was 6.

Example 3/Reaction without Catalyst in the Absence of Solvent 195 g of isostearyl alcohol (5,7,7-trimethyl 2-[1,3,3-trimethylbutyl]octanol-1 (trade name FO-180 available from NISSAN CHEMICAL INDUSTRIES, LTD., APHA=4)) and 410 g of isostearic acid (5,7,7-trimethyl 2-[1,33-trimethylbutyl]octanoic acid-1 (available from NISSAN CHEMICAL INDUSTRIES, LTD., APHA=8)) were placed in a stainless steel reactor, and reacted at 250° C. for 10 hours under nitrogen flow. As a result, 493 g of crude product of isostearyl isostearate (corresponding to Formula (1-3)) as a corresponding ester body was obtained. As a result of GC analysis, the amount of isostearyl isostearate was 66.4%, the amount of isostearyl alcohol was 0.6%, the amount of isostearic acid was 32.6%, and the total amount of other components was 0.4%. At that time, APHA was 77.

240 g of the crude product was purified by distillation using a molecular distillation device (Shibata-type falling film distillation device). The crude product was distilled at a temperature of 120° C. and a degree of reduced pressure of 0.6 to 0.8 Pa. As a result, 88 g of colorless transparent isostearyl isostearate as a fraction was obtained. APHA of the isostearyl isostearate was 13. In the residue, a coloration component mixed from the stainless steel reactor during the reaction remained, the residue was brown, and APHA thereof was 138.

Example 4/Reaction without Catalyst in the Absence of Solvent 151 g of 3,5,5-trimethylhexanol-1 (available from Tokyo Chemical industry Co., Ltd., APHA=3) and 311 g of isostearic acid (5,5,7-trimethyl 2-[1,3,3-trimethylbutyl]octanoic acid-1 (available from NISSAN CHEMICAL INDUSTRIES, LTD., APHA 8)) were placed in a stainless steel reactor, and reacted at 200 to 250° C. for 1.3 hours under nitrogen flow. As a result, 430 g of crude product of isononyl isostearate (corresponding to Formula (1-1)) as a corresponding ester body was obtained. As a result of GC analysis, the amount of isononyl isostearate was 78.0%, the amount of 3,3,5-trimethylhexanol-1 was 4.1%, the amount of isostearic acid was 17.6%, and the total amount of other components was 0.3%. At that time, APHA was 48.

101 g of the crude product was purified using a general distillation device. Isononyl isostearate was distilled at a temperature of 205° C. and a degree of reduced pressure of 0.1 Pa. The amount of the resultant colorless transparent isostearyl isostearate was 27 g. APHA was 14. In the residue in the reactor, a slight amount of coloration component mixed from the stainless steel reactor during the reaction remained, the residue in the reactor was yellow, and APHA thereof was 72.

(Analysis Result of Isononyl Isostearate Obtained in Example 4)

$^1$H-NMR (300 MHz, CDCl$_3$, δ ppm): 0.89-0.97; (36H, m), 1.02-1.15; (6H, m), 1.18-1.26; (2H, m), 1.34-1.53; (2H, m), 1.55-1.70; (4H, m), 1.73-2.19; (2H, m), 4.01-4.13; (2H, m) GC-MS (CI) m/z: 411.30 (M$^+$)

Example 5/Reaction without Catalyst in the Absence of Solvent 251 g of isostearyl alcohol (5,7,7-trimethyl 2-[1,3,3-trimethylbutyl]octanol-1 (trade name FO-180 available from NISSAN CHEMICAL INDUSTRIES, LTD., APHA=4)) and 154 g of 3,5,5-trimethylhexanoic acid-1 (available from Tokyo Chemical Industry Co., Ltd., APHA=4) were placed in a stainless steel reactor, and reacted at 200° C. for 4 hours under nitrogen flow. As a result, 382 g of crude product of isostearyl isononylate (corresponding to Formula (1-2)) as a corresponding ester body was obtained. As a result of GC analysis, the amount of isostearyl isononylate was 94.2%, the amount of isostearyl alcohol was 3.3%, the amount of 3,5,5-trimethylhexanoic acid-1 was 2.3%, and the total amount of other components was 0.2%. At that time, APHA was 44.

98 g of the crude product was purified using a general distillation device. Isostearyl isononylate was distilled at a temperature of 205° C. and a degree of reduced pressure of 0.1 Pa. The amount of the resultant colorless transparent isostearyl isononylate was 10 g. APHA was 8. In the residue in the reactor, a slight amount of coloration component mixed from the stainless steel reactor during the reaction remained, the residue in the reactor was yellow, and APHA thereof was 141.

(Analysis Result of Isostearyl Isononylate Obtained in Example 5)

$^1$H-NMR (300 MHz, CDCl$_3$, δ ppm): 0.83-0.95; (36H, m), 0.97-1.13; (6H, m), 1.15-1.33; (4H, m), 1.19-1.33; (2H, m), 1.43-1.74; (2H, m), 1.99-2.40; (2H, m), 3.89-4.06; (2H, m) GC-MS (CI) m/z: 411.25 (M$^+$)

Comparative Example 1/Reaction Using Catalyst in the Absence of Solvent

Isostearyl alcohol (5,7,7-trimethyl 2-[1,3,3-trimethylbutyl]octanol-1 (trade name FO-180 available from NISSAN CHEMICAL INDUSTRIES, LTD., APHA=4)) and isostearic acid (5,7,7-trimethyl 2-[1,3,3-trimethylbutyl]octanoic acid-1 (available from NISSAN CHEMICAL INDUSTRIES, LTD., APHA=8)) were reacted using p-toluene sulfonic acid as a catalyst at 120 to 150° C. in a glass lining reactor to synthesize isostearyl isostearate (corresponding to Formula (1-3)). As a result, a yellow crude product was obtained. At that time, APHA was 162. Even by distillation, a coloration component that seemed to be derived from a decomposed product of the catalyst was associated with distilled isostearyl isostearate and was not removed. APHA after distillation was 162, and the degree of coloration was larger as compared with Examples 1, 2, and 3.

Comparative Example 2/Reaction without Catalyst in the Absence of Solvent 200 g isostearyl alcohol (2-octyldecan-1-ol (trade name FO-180T available from NISSAN CHEMICAL INDUSTRIES, LTD., APHA=5)) and 221 g of isostearic acid (2-octhyldecanoic acid (trade name isostearic acid T, available from NISSAN CHEMICAL INDUSTRIES, LTD., APHA=10)) were placed in a stainless steel reactor, and reacted at 250° C. for 10 hours without a catalyst under nitrogen flow. As a result, 402 g of yellow crude product of isostearyl isostearate (corresponding to Formula (24)) as a corresponding ester body was obtained.

Formula (2-1)

As a result of GC analysis, the amount of isostearyl isostearate was 87.7%, the amount of isostearyl alcohol (2-octyldecan-1-ol) was 3.2%, the amount of isostearic acid (2-octyldecanoic acid) was 5.3%, and the total amount of other components was 3.8%. At that time, APHA was 191. Regardless of use of the same stainless steel reactor, the degree of coloration was larger as compared with Examples 1 and 3. This is considered because isostearyl alcohol (2-octyldecan-1-ol) and isostearic acid (2-octyldecanoic acid) as raw materials that are less branched and have relatively low thermal stability, and isostearyl isostearate as the product are exposed to high temperature and decomposed, resulting in coloration.

115 g of the crude product was purified by distillation. Isostearyl isostearate was distilled at a temperature of 270 to 280° C. and a degree of reduced pressure of 0.1 Pa. The amount of the resultant isostearyl isostearate was 4 g. APHA was 79. Regardless of distillation, the degree of coloration was larger as compared with Examples 1 and 3. This is considered because coloration derived from the raw materials and decomposed substance of the product cannot be removed by distillation. A certain amount of coloration component remained, the residue in the reactor was yellow, and APHA thereof was 260.

The invention claimed is:
1. A method for producing a multibranched aliphatic ester comprising
   reacting a multibranched aliphatic alcohol with a multibranched aliphatic carboxylic acid at a ratio of 1.01 to 2.5 mol of the carboxylic acid relative to 1 mol of the alcohol, while separating water produced by dehydration of an esterification reaction under nitrogen flow, in the absence of a solvent without a catalyst to obtain a multibranched aliphatic ester, and
   distilling the multibranched aliphatic ester to obtain a purified multibranched aliphatic ester,
   wherein
   at least one of the alcohol and the carboxylic acid is a $C_{10-30}$ compound,
   the obtained ester has a Hazen color number (APHA) of 1 to 30; and
   each of the multibranched aliphatic alcohol and the multibranched aliphatic carboxylic acid has a tertiary carbon atom and/or a quaternary carbon atom in the molecule and in which the total number of the tertiary carbon atom(s) and/or the quaternary carbon atom(s) in the molecule is 2 or more.

2. The method according to claim 1, wherein a multi-branched aliphatic $C_{10-30}$ alcohol is reacted with a multi-branched aliphatic $C_{7-30}$ carboxylic acid to obtain a multi-branched aliphatic $C_{17-60}$ ester.

3. The method according to claim 1, wherein a multi-branched aliphatic $C_{7-30}$ alcohol is reacted with a multi-branched aliphatic $C_{10-30}$ carboxylic acid to obtain a multi-branched aliphatic $C_{17-60}$ ester.

4. The method according to claim 1, wherein a multi-branched aliphatic $C_{10-30}$ alcohol is reacted with a multi-branched aliphatic $C_{10-30}$ carboxylic acid to obtain a multi-branched aliphatic $C_{20-60}$ ester.

5. The method according to claim 1, wherein the total number of the tertiary carbon atom(s) and/or the quaternary carbon atom(s) in the molecule is 2 to 10.

6. The method according to claim 1, wherein the multi-branched aliphatic alcohol is a monohydric alcohol.

7. The method according to claim 1, wherein the multi-branched aliphatic carboxylic acid is a monovalent carboxylic acid.

8. The method according to claim 1, wherein the reaction is carried out at a temperature in a range of from 180 to 300° C.

9. The method according to claim 1, wherein the Hazen color number (APHA) is 1 to 20.

10. The method according to claim 1, wherein the multibranched aliphatic alcohol is an alcohol selected from the group consisting of:

Formula A

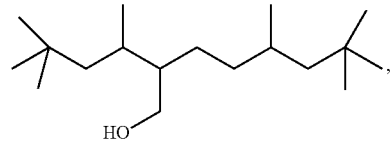

Formula B

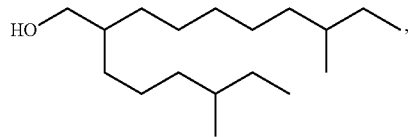

Formula C

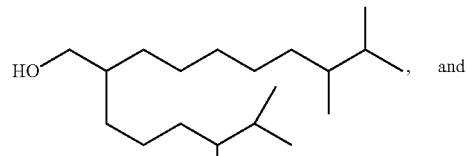

and

Formula D

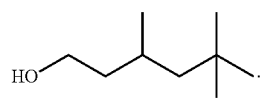

11. The method according to claim 1, wherein the multibranched aliphatic carboxylic acid is a carboxylic acid selected from the group consisting of:

Formula E

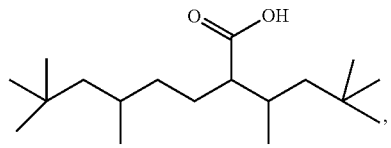

Formula F

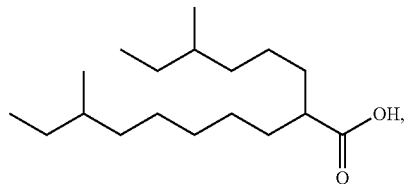

Formula G

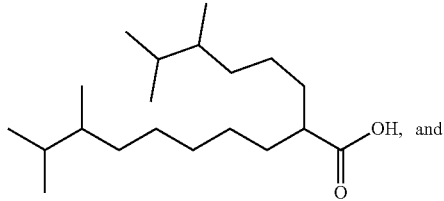

and

Formula H

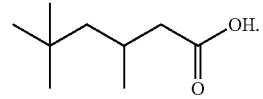

* * * * *